(12) United States Patent
Tanimoto et al.

(10) Patent No.: US 8,404,889 B2
(45) Date of Patent: Mar. 26, 2013

(54) PROCESS FOR PRODUCING ACROLEIN AND ACRYLIC ACID

(75) Inventors: Michio Tanimoto, Himeji (JP); Hideo Onodera, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 359 days.

(21) Appl. No.: 12/662,123

(22) Filed: Mar. 31, 2010

(65) Prior Publication Data

US 2010/0249455 A1 Sep. 30, 2010

(30) Foreign Application Priority Data

Mar. 31, 2009 (JP) ................................ 2009-084676

(51) Int. Cl.
*C07C 51/16* (2006.01)
*C07C 45/00* (2006.01)
(52) U.S. Cl. .................... 562/546; 562/547; 568/479
(58) Field of Classification Search .................. 562/547, 562/546; 568/479
See application file for complete search history.

(56) References Cited

U.S. PATENT DOCUMENTS

| 7,015,354 B2 | 3/2006 | Petzoldt et al. |
| 7,217,836 B2 | 5/2007 | Watanabe et al. |
| 2008/0228001 A1 | 9/2008 | Ogawa et al. |

FOREIGN PATENT DOCUMENTS

| JP | 2002-356450 | 12/2002 |
| JP | 2003-12589 | 1/2003 |
| JP | 2005-336085 | 12/2005 |
| JP | 2007-502254 | 2/2007 |

*Primary Examiner* — Taylor Victor Oh
(74) *Attorney, Agent, or Firm* — Wenderoth, Lind & Ponack, L.L.P.

(57) ABSTRACT

The invention offers an improvement in a process for start-up in the occasion of producing acrolein and acrylic acid by catalytically oxidizing propylene at vapor phase under high load conditions, the start-up meaning the step of increasing the propylene supply rate (loading) from the non-reacting condition to the prescribed reaction conditions. This process is characterized in that the propylene supply rate is increased in the start-up stage of the reaction until the prescribed composition of starting reactant gas and the flow rate of the starting reactant gas are obtained, while adjusting at least one of the reaction temperature, the composition of the starting reactant gas and flow rate of the starting reactant gas, so as to maintain the propylene conversion at not lower than 90 mol %, the maximum peak temperature of the catalyst layer in each reaction zone at no higher than 450° C., and the sum of each ΔT (maximum peak temperature of a catalyst layer—reaction temperature) at the catalyst layer in each of the reaction zones to be no more than 180° C., respectively. According to this process, the reaction speedily reaches the steady state (standard operating conditions) and a high acrolein and acrylic acid yield is stably achieved from the start of the reaction.

4 Claims, No Drawings

PROCESS FOR PRODUCING ACROLEIN AND ACRYLIC ACID

TECHNICAL FIELD

This invention relates to a process for producing acrolein and acrylic acid by catalytic vapor-phase oxidation of propylene or a propylene-containing gas with molecular oxygen or a molecular oxygen-containing gas, stably with high productivity or with high yield.

BACKGROUND ART

Acrylic acid is industrially important as a starting material for various synthetic resins, paints, plasticizing agents and the like, and is generally produced by two-stage oxidation method, in which propylene is catalytically oxidized at vapor phase to yield mainly acrolein, and the acrolein is successively catalytically oxidized at vapor phase to yield acrylic acid. In recent years, importance of acrylic acid as a starting material of water absorbent resins is constantly increasing. To cope with such increasing demand, a simple and general solution is to raise the productivity of acrylic acid by increasing the load of the starting material at the steady state (standard operating conditions) of the catalytic vapor-phase oxidation. Hence, also in the vapor-phase oxidation of propylene, which is the first stage reaction in the acrylic acid production by catalytic vapor-phase oxidation of propylene, similarly the operation under high starting material load is necessary.

The catalytic vapor-phase oxidation of propylene, however, is exothermic, and the calorific value also increases when the propylene load as the starting material is increased. Besides, during the period of start-up from the non-reacting condition up to immediately after attaining the prescribed reaction conditions, the catalytic activity is unstable, and when the propylene load is rapidly increased at the start-up, abnormal heat generation in the catalyst layer(s) is apt to occur to give rise to local heat-generating sites (hot spots), inviting in consequence reduction in the acrolein and acrylic acid yield due to the high temperature reaction and deterioration of the catalyst which is exposed to the high temperature. Such problems become even more serious when the vapor-phase oxidation is carried out under high load condition.

Thus, in the method of producing acrolein and acrylic acid by catalytic vapor-phase oxidation of propylene with molecular oxygen, a process enabling the production with higher stability and higher productivity or yield is in demand, and a number of proposals have been made also about contrivances for the start-up.

For example, the following patent documents 1, 2 and 3 disclose methods in which the supply amount per unit time of the starting material is kept low for a fixed period at the start-up stage of the reaction.

[Prior Art]
[Patent Documents]
  [Patent document 1] JP2003-12589A
  [Patent document 2] JP2005-336085A
  [Patent document 3] JP2007-502254T

SUMMARY OF THE INVENTION

Problems to be Solved by the Invention

In the process for producing acrolein and acrylic acid by catalytic vapor-phase oxidation of propylene under high load condition, during the period of start-up from the non-reacting condition until the prescribed reaction conditions are reached, the supply rate of propylene as the starting material is raised. When the propylene supply (load) is rapidly increased in this period, reduction in the acrolein and acrylic acid yields and deterioration of the catalyst are invited as above-described.

Whereas, when the low load condition (i.e., low starting material supply rate) is continued for a long time until the prescribed reaction conditions are reached as proposed in the patent documents 1, 2 and 3 to suppress abnormal heat generation at the catalyst layer(s), not only the acrolein and acrylic acid production rates during that period drop, but also activation of the catalyst becomes insufficient and its intrinsic performance cannot be fully exhibited after the prescribed reaction conditions are reached. Hence many hours are required until the stable, high catalytic performance is achieved. Furthermore, due to the unstable catalytic activity, in certain cases deterioration of the catalyst is invited by localized heat generation.

Also many proposals are made in recent years about the production process of acrolein and acrylic acid by catalytic vapor-phase oxidation of propylene using a fixed bed reactor in which catalysts are loaded in such a manner that plural reaction zones differing in catalytic activity are formed in the reaction tube(s). Where such a reactor comprising plural reaction zones is used, it is difficult to well balance the activity in each of the reaction zones during the start-up stage due to unstable catalytic activity, leading to a problem that the reaction rapidly advances at a part of the reaction zones and the catalyst in the particular zone(s) deteriorates due to the excessive heat generation.

Accordingly, therefore, the object of the present invention is to provide a start-up method whereby the steady state (standard operating conditions) of the reaction is quickly reached and a high acrolein and acrylic acid yields are stably achieved from the start of the reaction with less deterioration of the catalyst, even when a reactor of which reaction tube(s) are so loaded that plural reaction zones of different catalytic activity are formed therein is used.

Means for Solving the Problems

We have engaged in concentrative studies with the view to solve above problems, to discover: in the process for producing acrolein and acrylic acid by catalytic vapor-phase oxidation of propylene or a propylene-containing gas in the presence of molecular oxygen or a molecular oxygen-containing gas, the prescribed reaction conditions can be quickly reached and high acrolein and acrylic acid yields can be obtained stably from the very start of the reaction, by carrying out the start-up of the reaction while regulating the reaction conditions so as to secure the specific prescribed state of the reaction.

Thus, according to the present invention, a process for producing acrolein and acrylic acid by catalytic vapor-phase oxidation of propylene or a propylene-containing gas with molecular oxygen or a molecular oxygen-containing gas, using a fixed bed reactor which is loaded with the catalysts in such a manner that at least two layers of the reaction zones having different activity are formed in the axial direction of each of the reaction tubes, is provided, which process is characterized in that the propylene supply rate is increased in the start-up stage of the reaction until the prescribed composition of the starting reactant gas and the flow rate of the starting reactant gas are attained, while adjusting at least one of the reaction temperature, the composition of the starting reactant gas and the flow rate of the starting reactant gas, so as to maintain the propylene conversion at not lower than 90 mol %, the maximum peak temperature of the catalyst layer in each reaction zone at no higher than 450° C., and the sum of each ΔT (maximum peak temperature of a catalyst layer—reaction temperature) at the catalyst layer in each of the reaction zones to be no more than 180° C., respectively.

[Effect of the Invention]

According to the present invention as described in the above, in the occasion of producing acrolein and acrylic acid by catalytic vapor-phase oxidation of propylene or a propylene-containing gas with molecular oxygen or a molecular oxygen-containing gas using a fixed bed reactor which is loaded with the catalysts in such a manner that at least two layers of the reaction zones having different activity are formed in the axial direction of each of the reaction tubes, the start-up can be carried out within a short time. In consequence it becomes possible to quickly attain the prescribed reaction conditions, to prevent deterioration of the catalyst due to overheat at the start-up time and, furthermore, to obtain acrolein and acrylic acid stably at high yield from the start of the reaction.

THE BEST EMBODIMENTS FOR CARRYING OUT THE INVENTION

Hereinafter the process for producing acrolein and acrylic acid of the present invention is explained in details, it being understood that the scope of the invention is not limited by the explanation given in the following but the invention can be suitably modified and put to practice within a scope not impairing the purpose of the present invention.

The process of the present invention concerns production of acrolein and acrylic acid by catalytic vapor-phase oxidation of propylene or a propylene-containing gas with molecular oxygen or a molecular oxygen-containing gas, using a fixed bed reactor which is loaded with the catalysts in such a manner that at least two layers of the reaction zones having different catalytic activity are formed in the axial direction of each of the reaction tubes, the process being characterized in that the propylene supply rate is increased in the start-up stage of the reaction until the prescribed composition of the starting reactant gas and the flow rate of the starting reactant gas are attained, while adjusting at least one of the reaction temperature, the composition of the starting reactant gas and the flow rate of the starting reactant gas, so as to maintain the propylene conversion at not lower than 90 mol %, the maximum peak temperature of the catalyst layer in each reaction zone at no higher than 450° C., and the sum of each ΔT (maximum peak temperature of a catalyst layer—reaction temperature) at the catalyst layer in each of the reaction zones to be no more than 180° C., respectively.

The catalysts useful for the present invention are subject to no particular limitation, so long as they are catalysts for production of acrolein and acrylic acid by catalytic vapor-phase oxidation of propylene or a propylene-containing gas with molecular oxygen or a molecular oxygen-containing gas, and any of heretofore known oxide catalysts can be used. More specifically, those oxide catalysts comprising the catalytically active ingredients as represented by the following general formula (1) can be conveniently used:

$$Mo_{12}Bi_aFe_bA_cB_dC_eD_fO_x \quad (1)$$

(wherein Mo is molybdenum, Bi is bismuth, Fe is iron, A is at least one element selected from the group consisting of cobalt and nickel, B is at least one element selected from the group consisting of alkali metals, alkaline earth metals and thallium, C is at least one element selected from the group consisting of tungsten, silicon, aluminum, titanium and zirconium, D is at least one element selected from the group consisting of phosphorus, tellurium, antimony, tin, cerium, lead, niobium, manganese, arsenic and zinc, O is oxygen, and a, b, c, d, e, f and x respectively denote atomic ratios of Bi, Fe, A, B, C, D and O wherein $0<a\leq10$, $0<b\leq20$, $2\leq c\leq20$, $0<d\leq10$, $0\leq e\leq30$, $0\leq f\leq4$, and x is a value determined according to the state of oxidation of each of the elements).

There is no particular limitation also as to the shape of the catalyst, which may be spherical, columnar, ring-formed or amorphous. Obviously, "spherical" does not mean true spheres but substantially spherical shape is satisfactory. This applies also to columnar and ring forms.

The method for preparing the catalyst is again subject to no particular limitation, and any of heretofore known methods may be used. As the molding method, extrusion molding, tabletting, Malmerizer method, granulation (tumbling granulation and centrifugal flow coating), impregnation, evaporation to dryness or the like can be adopted. While these methods can be suitably selected and used in combination, granulation method for having an optional inert carrier of a fixed shape carry the catalytically active components is preferred. More concretely, as the inert carrier, carriers having a prescribed shape made of, for example, alumina, silica, silica-alumina, titania, magnesia, steatite, silicon carbide and the like can be used.

In the present invention, it is preferred to use as the fixed bed reactor which is loaded with the catalysts in such a manner that at least two layers of the reaction zones differing in activity are formed in the axial direction of each of the reaction tubes, a fixed bed reactor which is so loaded with the catalysts that the catalytic activity in the reaction zones is successively increased from the inlet side of the reaction gas toward the outlet side. As the means for varying the activity for each reaction zone, known techniques can be used. For instance, changing the amount of alkali metal added [JP63 (1988)-38331B], changing the volume occupied by the catalyst [JP7 (1995)-84400B], or changing the supported rate of catalytically active component (weight ratio of the active substance per catalyst) [JP10 (1998)-168003A] have been proposed. The length of each reaction zone is suitably determined to allow the catalyst selected as above to exhibit its maximum effect. Generally the length of the catalyst-loaded reaction zone at the inlet side of the reaction gas occupies 10-80% of the total length of the catalyst layer, preferably 15-70%. The catalyst to be loaded in each reaction zone may be the same or different in composition or shape, and may be a molded catalyst formed by giving a fixed shape to the catalytic component, a carried catalyst formed of an optional inert carrier having a fixed shape and the catalytic component carried thereon, or a combination of such molded catalyst and carried catalyst. It is generally preferred to load one and same reaction zone with a molded catalyst or carried catalyst of the same composition and same shape.

The reactor useful for the present invention is subject to no particular limitation, it being satisfactory that the reactor is adapted to in-tube loading system wherein solid particles (catalyst particles, inert particles or the like) are loaded into the reaction tubes, and at least one of the reaction tube(s) is equipped with a device for measuring the temperature of solid particle layers. In industrial scale production of acrylic acid, known shell-and-tube reactor such as single reactor, tandem reactor and the like can be suitably utilized. In particular, a shell-and-tube reactor designed to serve also as a heat exchanger is advantageously used in the present invention, for controlling removal or supply of heat. In such a shell-and-tube reactor the supply gas is introduced into the reaction tubes which are loaded with the solid particles and the reaction product (inclusive of intermediate product) is discharged. On the other hand, a heating medium (shell-side fluid) is flowed through the spaces between the tubes, exchanging heat with the reaction tubes to maintain a prescribed reaction temperature. The term, reaction temperature, as used in this specification means the heating medium temperature at the inlet into the reactor or reaction zone.

The device to be used in the reaction tube for the temperature measurement is not particularly limited, but any known device can be suitably utilized according to the purpose of use. As examples of suitable temperature measuring device, a thermocouple (thermometer) equipped with a temperature detection part for measuring the temperature in the reaction tube, resistance thermometer and the like can be named. For the "temperature measuring device" to be used in the present invention, it is satisfactory to have at least a temperature detection part, while a freely mobile type in the axial direction of the reaction tube is preferred, to enable it to detect the maximum peak temperature at the catalyst layer(s). For a shell-and-tube reactor, preferably plural reaction tubes for the measurement are provided among the bundle of reaction tubes, to grasp the temperature distribution throughout the inside of the reactor. As each $\Delta T$ (maximum peak temperature of the catalyst layer—reaction temperature) of the catalyst layer in each of the reaction zones in that case, the highest value measured in the plural reaction tubes is adopted.

The starting material for the reaction used in this invention is propylene or a propylene-containing gas. The process of this invention is important as the first stage for production of acrylic acid by two-stage catalytic vapor-phase oxidation using propylene as the starting material. The acrolein-containing gas as obtained in the first stage can be used in the acrolein-oxidizing second stage as it is, or after separating the acrolein to which oxygen, steam or other gas(es) are added where necessary.

In the process for producing acrolein and acrylic acid using propylene or a propylene-containing gas as the starting material and catalytically oxidizing the same at vapor phase with molecular oxygen or a molecular oxygen-containing gas, according to the present invention, the reaction conditions are subject to no particular limitation so far as they meet the purpose of the invention, and those conditions generally used for this type of reaction can be adopted.

For example, in the reaction for producing acrolein and acrylic acid from propylene, a gaseous mixture of 1-15 vol %, preferably 4-12 vol %, of propylene; 0.5-25 vol %, preferably 2-20 vol % of molecular oxygen; 0-30 vol %, preferably 0-25 vol % of steam and the balance of an inert gas such as nitrogen, is used as the starting gas which is contacted with an oxidation catalyst at a temperature range of 280-430° C., preferably 280-400° C., under the reaction pressure ranging 0.1-1.0 MPa. The present invention is particularly effective for the reaction under high propylene load condition. That is, the invention is effective for the start-up of the reaction which is performed under the setting for the steady state (standard operating conditions) of the propylene space velocity of at least 110 $hr^{-1}$ (STP), preferably at least 120 $hr^{-1}$ (STP). While depending more or less on the catalysts used, generally the propylene space velocity exceeding 600 $hr^{-1}$ (STP), in many cases 300 $hr^{-1}$ (STP), is undesirable because sufficient catalytic performance cannot be exhibited due to the heat generated from the reaction.

When the starting propylene supply is rapidly increased at the start-up stage under such high load condition, occasionally the maximum peak temperature of the catalyst layer exceeds 450° C. as the starting material supply rate reached around 85% of the standard operating conditions, accompanying the rapid rise in the supply rate of the starting material. According to the present invention, the amount of propylene supply is increased, while checking the temperature change in the catalyst layers and adjusting at least one factor of the reaction temperature, composition of the starting reactant gas and flow rate of the starting reactant gas, until the prescribed composition and flow rate of the starting gas are reached. In that occasion, it is necessary to so control the operation as to keep the maximum peak temperature of the catalyst layers at no higher than 450° C., and the sum of each $\Delta T$ (maximum peak temperature—reaction temperature) at the catalyst layer in each of the reaction zones, to be no more than 180° C., respectively.

Higher propylene conversion is generally advantageous from the viewpoint of productivity, so long as it is not accompanied by drop in the acrolein and acrylic acid yield due to high temperature reaction and catalyst deterioration caused by its exposure to high temperatures. It is recommendable to maintain the conversion of at least 90%, preferably at least 95%, inter alia, at least 97%, even at the start-up stage. Here the propylene conversion and acrolein and acrylic acid yield can be monitored by continuously sampling the gas at the inlet of the reactor and the gas at the outlet of the reactor and analyzing them by online gas chromatography.

In increasing the amount of the propylene supply (load) up to the prescribed condition (target value) according to the invention, the reaction temperature, composition of the starting reactant gas and flow rate of the starting reactant gas are adjusted as follows, while monitoring the maximum peak temperature of the catalyst layers and $\Delta T$ at the catalyst layer in each reaction zone. Thus it is made possible to bring about the steady state (standard operating conditions) within a short time, not adversely affecting the catalytic performance.

Adjustment of the Reaction Temperature

Where there are two reaction zones, for example, the following situation (1) or (2) can be envisioned as to $\Delta T$ at the catalyst layers. Accordingly, the maximum peak temperature of the catalyst layers and $\Delta T$ at the catalyst layer in each reaction zone are adjusted.

(1) $\Delta T$ at the first layer>$\Delta T$ at the second layer (2) $\Delta T$ at the first layer<$\Delta T$ at the second layer Prevention of the maximum peak temperature of the catalyst layers from rising higher than 450° C. is achieved by lowering the reaction temperature in above case (1), and by raising the reaction temperature in case (2), balancing $\Delta T$ at the first layer with $\Delta T$ at the second layer. The starting material supply rate is further increased within a range not rendering the sum of $\Delta T$'s at the first layer and the second layer more than 180° C. These adjustments of the reaction temperature for the purpose of keeping the maximum peak temperature of the catalyst layers and the sum of $\Delta T$'s at the catalyst layers in the reaction zones within the prescribed ranges can be effected either under a fixed supply rate or increasing the supply rate, of the starting material.

Adjustments of the Composition and Flow Rate of the Starting Reactant Gas

While depending also on the capacity of individual oxidation apparatus or the process used, generally modification of the reaction conditions is possible to a certain extent. Hence, rise in the maximum peak temperature of the catalyst layers exceeding 450° C. can be prevented by changing the propylene concentration, oxygen/propylene ratio or steam concentration in the starting gas, while balancing the $\Delta T$ at the first layer with $\Delta T$ at the second layer. The starting material supply rate is further increased within a range not rendering sum of $\Delta T$'s at the first layer and the second layer more than 180° C. These adjustments of the composition of the starting reactant gas for the purpose of keeping the maximum peak temperature of the catalyst layers and the sum of ΔT's at the catalyst layers in the reaction zones within the prescribed ranges can be effected either under a fixed supply rate or increasing supply rate of the starting material.

In a shell-and-tube reactor, in occasions the reaction tubes in which ΔT's fall under the situation (1) and those in which ΔT's fall under situation (2) are present within a same reactor, particularly at the start-up time or high load reaction time, due to temperature distribution of the heating medium throughout the whole reactor or scattering in the catalyst loading. In such a case also it is sufficient to increase the propylene supply rate until the prescribed composition and flow rate of the starting reactant gas are attained, while adjusting at least one of the reaction temperature, composition of the starting reactant gas and flow rate of the starting reactant gas, so that all of the reaction tubes for the temperature measuring should fulfill the standards set by the present invention. In that occasion, when the sum of each ΔT (maximum peak temperature of the catalyst layer—reaction temperature) at the catalyst layers in each of the reaction zones is going to exceed 180° C., the starting material supply rate cannot be further increased at that time point. When the sum of ΔT's starts to show a lowering tendency, the enhancement in the starting material supply rate can be resumed, whereby enabling to get to steady state (standard operating conditions) within a very short time.

In the process for producing acrylic acid by two-stage oxidation of propylene, simultaneously with the start-up of the first stage catalytic vapor-phase oxidation of propylene (hereafter referred to as "first-stage reaction"), the second stage catalytic vapor-phase oxidation of acrolein (hereafter referred to as "second-stage reaction") starts up. Therefore, when the present invention is applied to the first-stage reaction, it is necessary to carefully watch the maximum peak temperature at the catalyst layers also in the second-stage reaction. Where a reactor loaded with catalysts in such a manner that plural reaction zones differing in catalytic activity are formed is used in the second-stage reaction, the sum of each ΔT (maximum peak temperature of catalyst layer—reaction temperature) at the catalyst layer(s) in each reaction zone must also be carefully monitored. It is preferred to increase the propylene supply until the prescribed composition of the starting reactant gas and the flow rate of the starting reactant gas are reached while controlling at least one of the reaction temperature, the composition of the starting reactant gas and the flow rate of the starting reactant gas, so as to maintain the maximum peak temperature of all the catalyst layers at no higher than 400° C. and the sum of each ΔT at the catalyst layer in each of the reaction zones to be no more than 150° C., respectively, in the second-stage reaction as well as in the first-stage reaction.

EXAMPLES

Hereinafter the present invention is more specifically explained referring to Examples, it being understood that the invention is in no way restricted thereby. In the following, "mass parts" may be simply indicated as "parts" for the sake of convenience. The propylene conversion and acrolein and acrylic acid yield were calculated according to the following equations.

Propylene conversion (mol %) =

(mol number of reacted propylene/mol number of supplied propylene) × 100

Acrolein and acrylic acid yield (mol %) =

(mol number of produced acrolein and acrylic acid/mol number of supplied propylene) × 100

Acrylic acid yield (mol %) = (mol number of produced acrylic acid/mol number of supplied propylene) × 100

Example 1

[Preparation of Catalyst 1]

In 500 parts of iron-exchange water, 275 parts of cobalt nitrate and 110 parts of nickel nitrate were dissolved. Separately, 114 parts of ferric nitrate and 165 parts of bismuth nitrate were dissolved in an aqueous solution formed of 80 parts of 61 wt % nitric acid and 300 parts of ion-exchange water. Again separately, into 1500 parts of heated ion-exchange water, 400 parts of ammonium paramolybdate and 10.2 parts of ammonium paratungstate were added and dissolved under stirring. To the resultant aqueous solution, the two separately prepared aqueous solutions as above were added dropwise and mixed, into which an aqueous solution of 1.9 parts of potassium nitrate as dissolved in 30 parts of ion-exchange water was added to provide a suspension. The suspension was heated, stirred and evaporated, and the resulting dry matter was dried at 200° C. and pulverized to a size not greater than 150 μm to provide a catalyst powder. Into a tumbling granulator 1500 parts of spherical alumina carrier of 4.0 mm in average particle diameter was fed, and then the catalyst powder was slowly fed thereinto together with 35 mass % of aqueous ammonium nitrate solution as a binder, to have the carrier support the catalyst, followed by 6 hours' heat treatment at 470° C. in an atmosphere of air. Thus catalyst 1 was obtained. The composition of the metal elements excluding oxygen and the carrier was as follows:

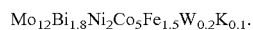

$Mo_{12}Bi_{1.8}Ni_2Co_5Fe_{1.5}W_{0.2}K_{0.1}$.

The supported rate of the catalyst 1 as calculated by the following equation was about 31 mass %.

Supported rate (mass %)=(mass of supported catalyst powder/mass of the carrier used)×100

[Preparation of Catalyst 2]

Catalyst 2 was prepared similarly to catalyst 1 except that spherical alumina carrier of 6.0 mm in average particle diameter was used. The supported rate of catalyst 2 was about 31 mass %.

[Reactor]

A reactor composed of a steel reaction tube of 3000 mm in total length and 25 mm in inner diameter, a shell for passing a heating medium therethrough and for covering the reaction tube, and a temperature measuring device comprising a thermocouple having a temperature-detection part for measuring temperature in the reaction tube, said thermocouple being freely mobile along the axial direction in the tube, was set vertically, and the temperatures of the catalyst layers were regularly monitored. From the top of the reactor the catalyst 2 and catalyst 1 were successively dropped to form the first reaction zone (a catalyst layer loaded with catalyst 2) and the second reaction zone (a catalyst layer loaded with catalyst 1), the respective layer lengths in the reaction zones being 900 mm and 2000 mm. The propylene conversion and acrolein and acrylic acid yield were monitored by continuously sampling the gas at the inlet of the reactor and that at the outlet of the reactor and analyzing them by online gas chromatography.

[Oxidation]

The temperature of the heating medium was maintained at 325° C., and into the catalyst-loaded reaction tube a gaseous mixture of 1.27 m³ of air (STP)/hr, 0.580 m³ of nitrogen (STP)/hr and 0.273 m³ of steam (STP)/hr was supplied from the bottom end of the reactor. Subsequently propylene supply was started in such a manner as to attain its supply rate of 0.133 m³ (STP)/hr after 2.5 hours. The composition of the reactant gas at that time was: propylene 5.9 vol %, oxygen 11.8 vol %, steam 12.1 vol %, and the balance of an inert gas such as nitrogen. The propylene conversion was 97.8% and the acrolein and acrylic acid yield was 93.9%. The respective maximum peak temperatures of the catalyst layers in the reaction zones were 388° C. in the first reaction zone, and 370° C. in the second reaction zone, and the sum of each ΔT at the catalyst layer in each of the reaction zones was 108° C.

Then the temperature of the heating medium was changed to 330° C. In the course of gradually increasing propylene and air supplies and gradually decreasing nitrogen supply, when the respective flow rates became 0.156 m³ (STP)/hr of propylene, 1.47 m³ (STP)/hr of air and 0.361 m³ (STP)/hr of nitrogen, the maximum peak temperature of the catalyst layer in the second reaction zone was 388° C., but that of the catalyst layer in the first reaction zone rose to 425° C. and was about to exceed 450° C. Whereupon the temperature of the heating medium was changed to 320° C. Up to that time about 25 hours had passed since the initiation of propylene supply, and the composition of the reactant gas at that time was: propylene: 6.9 vol %, oxygen 13.6 vol %, steam 12.1 vol %, and the balance of an inert gas such as nitrogen. The propylene conversion was 98.1%, and the acrolein and acrylic acid yield was 94.2%. The maximum peak temperature of the catalyst layer in the first reaction zone temporarily rose up to 430° C., and the sum of each ΔT at the catalyst layer in each of the reaction zones was 158° C.

In the course of increasing the propylene and air supplies and decreasing the nitrogen supply, while maintaining the heating medium temperature of 320° C., when the respective flow rates became 0.181 m³ (STP)/hr of propylene, 1.70 m³ (STP)/hr of air and 0.099 m³ (STP)/hr of nitrogen, the propylene conversion was about the drop below 90%. Accordingly, after 42 hours of the operation the nitrogen flow rate was further decreased to 0.050 m³ (STP)/hr, the heating medium temperature was changed to 325° C. and the propylene supply was increased. At the end of 46 hours of the operation, the propylene supply rate was 0.186 m³ (STP)/hr and the composition of the starting reactant gas was: propylene 8.4 vol %, oxygen 16.1 vol %, steam 12.3 vol % and the balance of an inert gas such as nitrogen. The propylene conversion was 98.2%, acrolein and acrylic acid yield was 94.3%, the respective maximum peak temperatures were 410° C. in the first reaction zone and 380° C. in the second reaction zone, and the sum of each ΔT at the catalyst layer in each of the reaction zones was 140° C.

Further increasing the propylene supply rate up to the target value of 0.198 m³ (STP)/hr, the prescribed reaction conditions were reached to complete the start-up. The composition of the reactant gas was: propylene 8.7 vol %, oxygen 15.7 vol %, steam 12.0 vol %, and the balance of an inert gas such as nitrogen.

Throughout the start-up stage, the propylene conversion of at least 90 mol % was maintained, the maximum peak temperatures of the catalyst layers in both of the reaction zones were maintained below 450° C., and the sum of each ΔT at the catalyst layer in each of the reaction zones were maintained below 180° C.

Sixty (60) hours had passed from the initiation of propylene supply when the start-up was completed. The propylene conversion then was 98.0%, acrolein and acrylic acid yield was 94.1%, temperature of the heating medium was 326° C., the respective maximum peak temperatures of the catalyst layers in the first and second reaction zones were 413° C. and 385° C., and the sum of each ΔT at the catalyst layer in each of the reaction zones was 146° C.

Thereafter the steady state (standard operating conditions) was maintained while controlling the temperature of the heating medium to keep the propylene conversion of at least 97%, and the reaction was continued for 4,000 hours. After the 4000 hours passed, the temperature of the heating medium was 333° C., the respective maximum peak temperatures in the catalyst layers in the first and second reaction zones were 415° C. and 393° C., the sum of each ΔT at the catalyst layer in each of the reaction zones was 142° C., propylene conversion was 97.9%, and the acrolein and acrylic acid yield was 93.5%.

The data collected in the reaction procedure as described in Par. [0031] to Par. [0037] are shown in the following table.

TABLE

| Time passed (hr) | Reaction Temp. (°C) | Peak 1 °C | Peak 2 °C | ΔT Total °C | Propylene Conversion % | Combined Yield % | Propylene Supply rate m³/hr | Propylene Composition % | Air Supply Rate m³/hr | Air Oxygen composition % | Steam Supply rate m³/hr | Steam Composition % | Nitrogen Supply Rate m³/hr | Total Flow Rate m³/hr | Propylene Space Velocity hr⁻¹ | Note (Corresponding Par's in Specification) |
|---|---|---|---|---|---|---|---|---|---|---|---|---|---|---|---|---|
| 0 | 325 | | | | | | 0 | 0 | 1.27 | 12.5 | 0.273 | 12.8 | 0.580 | 2.123 | 0 | [0031] |
| 2.5 | 325 | 388 | 370 | 108 | 97.8 | 93.9 | 0.133 | 5.9 | 1.27 | 11.8 | 0.273 | 12.1 | 0.580 | 2.256 | 94 | |
| about 25 | 330 | 425 | 388 | 153 | | | 0.156 | 6.9 | 1.47 | 13.6 | 0.273 | 12.1 | 0.361 | 2.260 | 110 | [0032] |
| | 330→320 | 430 | 388 | 158 | 98.1 | 94.2 | 0.156 | 6.9 | 1.47 | 13.6 | 0.273 | 12.1 | 0.361 | 2.260 | 110 | |
| 42 | 320→325 | | | | | | 0.181 | 8.0 | 1.70 | 15.8 | 0.273 | 12.1 | 0.099 0.050 | 2.253 | 127 | [0033] |
| 46 | 325 | 410 | 380 | 140 | 98.2 | 94.3 | 0.186 | 8.4 | 1.70 | 16.1 | 0.273 | 12.3 | 0.050 | 2.209 | 131 | [0034] → [0036] [0037] |
| 60 | 326 | 413 | 385 | 146 | 98.0 | 94.1 | 0.198 | 8.7 | 1.70 | 15.7 | 0.273 | 12.0 | 0.099 | 2.270 | 139 | |
| 4000 | 333 | 415 | 393 | 142 | 97.9 | 93.5 | | | | | | | | | | |

Comparative Example 1

The reaction was initiated in the manner similar to Example 1 and in the course of increasing the propylene and air supplies and decreasing nitrogen supply, at the point of time when the respective flow rates reached 0.156 m³ (STP)/hr of propylene and 1.47 m³ (STP)/hr of air and 0.361 m³ (STP)/hr of nitrogen, the maximum peak temperature of the catalyst layer in the second reaction zone was 388° C. but that in the first reaction zone rose to 425° C. and was about to exceed 450° C. The propylene supply however was maintained at the same rate, and the maximum peak temperature of the catalyst layer in the first reaction zone reached 460° C. By that time about 25 hours had passed since the initiation of propylene supply, whereat the propylene conversion was 98.3%, the respective maximum peak temperatures of the catalyst layers in the first and second reaction zones were 460° C. and 374° C., and the sum of each ΔT at the catalyst layers in the reaction zones was 174° C.

Thereafter the propylene supply rate was increased up to the target value of 0.198 m³ (STP)/hr similarly to Example 1 to attain the prescribed reaction conditions and the start-up was completed. By that time about 80 hours had passed since the initiation of propylene supply, and at which time the propylene conversion was 97.9%, acrolein and acrylic acid yield was 93.8%, the heating medium temperature was 327° C., the maximum peak temperatures of the catalyst layers in the first and second reaction zones were 409° C. and 393° C., respectively, and the sum of each ΔT at the catalyst layer in each of the reaction zones was 148° C.

Subsequently the steady state (standard operating conditions) was maintained while controlling the heating medium temperature to keep the propylene conversion of at least 97% and the reaction was continued for 4000 hours in total. After the 4000 hours had passed, the heating medium temperature was 345° C., the maximum peak temperatures of the catalyst layers in the first and second reaction zones were 416° C. and 417° C., respectively, and the sum of each ΔT at the catalyst layer in each of the reaction zones was 143° C. The propylene conversion was 98.4% and acrolein and acrylic acid yield was 92.9%. Compared with Example 1, the rising rate of the heating medium temperature with time passage was high and the catalytic performance was low.

Comparative Example 2

The reaction was initiated in the manner similar to Example 1 and in the course of increasing the propylene and air supplies and decreasing nitrogen supply, at the point of time when the respective flow rates became 0.181 m³ (STP)/hr of propylene, 1.70 m³ (STP)/hr of air and 0.099 m³ (STP)/hr of nitrogen, the propylene conversion was about to drop below 90% but the propylene supply rate was kept being increased. After 46 hours of the operation, the propylene supply rate was 0.186 m³ (STP)/hr, and the composition of the reactant gas was: propylene 8.3 vol %, oxygen 15.8 vol %, steam 12.1 vol % and the balance of an inert gas such as nitrogen. The propylene conversion was 94.4%, acrolein and acrylic acid yield was 90.7%, the respective maximum peak temperatures of the catalyst layers in the first and second reaction zones were 385° C. and 406° C. and the sum of each ΔT at the catalyst layer in each of the reaction zones was 151° C. Thereafter the propylene supply rate was increased up to the target value of 0.198 m³ (STP)/hr similarly to Example 1 to attain the prescribed reaction conditions and the start-up was completed. During the start-up, the temperature behaviors at the catalyst layers were unstable compared with those in Example 1 and more time was required for maintaining the respective maximum peak temperatures of the catalyst layers in the reaction zones at not higher than 450° C. and the sum of each ΔT (maximum peak temperature of catalyst layer—reaction temperature) at the catalyst layer in each of the reaction zones, to be not more than 180° C. Thus about 145 hours were consumed before the start-up was completed.

Example 2

[Preparation of Catalyst 3]

In 600 parts of ion-exchange water, 412 parts of cobalt nitrate and 55 parts of nickel nitrate were dissolved. Separately, 153 parts of ferric nitrate and 229 parts of bismuth nitrate were dissolved in an aqueous nitric acid solution composed of 100 parts of 61 wt % nitric acid and 350 parts of ion-exchange water. Again separately, 500 parts of ammonium paramolybdate and 6.4 parts of ammonium paratungstate were added to 2000 parts of heated ion-exchange water and dissolved under stirring. To the resultant aqueous solution, the two separately prepared aqueous solutions were added dropwise, mixed, and to which 2.4 parts of potassium nitrate as dissolved in 50 parts of ion-exchange water was added to provide a suspension. The resulting suspension was heated, stirred and evaporated. Thus obtained dry matter was dried at 200° C. and pulverized to a size not greater than 150 μm, to provide a catalyst powder. Into a tumbling granulator 2050 parts of spherical alumina carrier of 4.0 mm in average particle diameter was fed, and then the catalyst powder was slowly fed thereinto, together with 35 mass % of aqueous ammonium nitrate solution as a binder, to have the carrier support the catalyst, followed by 6 hours' heat treatment at 475° C. in an atmosphere of air. Thus catalyst 3 was obtained. The supported rate of this catalyst 3 was about 30 mass %, and the composition of the metal elements excluding oxygen and the carrier was as follows:

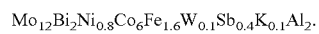

$Mo_{12}Bi_2Ni_{0.8}Co_6Fe_{1.6}W_{0.1}Sb_{0.4}K_{0.1}Al_2$.

[Preparation of Catalyst 4]

Catalyst 4 was prepared similarly to catalyst 3 except that spherical alumina carrier of 6.0 mm in average particle diameter was used. The supported rate of catalyst 4 was about 30 mass %.

[Reactor]

Into a reactor composed of 24 steel reaction tubes of each 3000 mm in total length and 25 mm in inner diameter and a shell which covered them and through which the heating medium was passed, the catalyst 4 and catalyst 3 were successively dropped from the top of the reactor to form the first reaction zone (the catalyst layer loaded with catalyst 4) and the second reaction zone (the catalyst layer loaded with catalyst 3). The respective lengths of the catalyst layers in the reaction zones were 900 mm and 2000 mm. A temperature measuring device comprising a thermocouple having a temperature detection part for measuring the temperature inside the reaction tube and being adapted to freely move along the axial direction in the reaction tube, was installed on six of the reaction tubes, to constantly monitor the catalyst layer temperatures. The propylene conversion and acrolein and acrylic acid yield were monitored by continuously sampling the gas at the inlet of the reactor and that at the outlet of the reactor and analyzing them by online gas chromatography.

[Oxidation]

Maintaining the temperature of the heating medium at 317° C., into the catalyst-loaded reaction tubes a gaseous mixture of 30.5 m³ (STP)/hr of air, 13.9 m³ (STP)/hr of nitrogen and 6.5 m³ (STP)/hr of steam was supplied from the bottom end of the reactor. Subsequently propylene supply was started in such a manner as to attain its supply rate of 3.6 m³ (STP)/hr after 3 hours. The composition of the reactant gas at that time was: propylene 6.6 vol %, oxygen 11.7 vol %, steam 12 vol %, and the balance of an inert gas such as nitrogen. The propylene conversion was 97.6% and the acrolein and acrylic acid yield was 93.5%. The respective maximum peak temperatures of the catalyst layers in the reaction zones were 380° C. in the first reaction zone, and 376° C. in the second reaction zone, and the sum of each ΔT at the catalyst layer in each of the reaction zones was 122° C.

Then the temperature of the heating medium was changed to 320° C. In the course of gradually increasing the propylene and air supplies and decreasing nitrogen supply, when the respective flow rates became 3.8 m³ (STP)/hr of propylene, 35.2 m³ (STP)/hr of air and 8.7 m³ (STP)/hr of nitrogen, in some of the reaction tubes the maximum peak temperature in the second reaction zones rose up to 410° C., and the sum of each ΔT in the catalyst layer in each of the reaction zones temporarily rose to 161° C. and was about to exceed 180° C. Whereupon the heating medium temperature was changed to 325° C. By that time about 50 hours had passed since the initiation of propylene supply. The composition of the reactant gas then was: propylene 7.4 vol %, oxygen 13.5 vol %, steam 12 vol %, and the balance of an inert gas such as nitrogen. The propylene conversion was 98.2% and acrolein and acrylic acid yield was 94.1%. The maximum peak temperature in the second reaction zone was 404° C., and that in the first reaction zone was 403° C.

While maintaining the heating medium temperature at 325° C. the propylene supply rate was raised to 4.3 m³ (STP)/hr. At 80 hours after the initiation of propylene supply, the maximum peak temperature of the catalyst layer was 406° C. and the sum of each ΔT at the catalyst layer of each of the reaction zones was 160° C. Further increasing the propylene supply rate to the target value of 4.5 m³ (STP)/hr and rendering the air supply rate and nitrogen supply rate 39.0 m³ (STP)/hr and 4.5 m³ (STP)/hr, respectively, the prescribed reaction conditions were reached and the start-up was completed. During the start-up stage, the propylene conversion was maintained at not lower than 90 mol %, the maximum peak temperature of the catalyst layer in each of the reaction zones was kept at not higher than 450° C. and the sum of each ΔT at the catalyst layer in each of the reaction zones, not more than 180° C. By the time of the start-up completion, 100 hours had passed since the initiation of propylene supply, at which time the heating medium temperature was 326° C. and the composition of the reactant gas was: propylene 8.3 vol %, oxygen 15.0 vol %, steam 12 vol % and the balance of an inert gas such as nitrogen. The propylene conversion was 97.7%, acrolein and acrylic acid yield was 93.6%, the respective maximum peak temperatures of the catalyst layers in the first reaction zone and the second reaction zone were 405° C. and 406° C., and the sum of each ΔT at the catalyst layer in each of the reaction zones was 159° C.

Comparative Example 3

The reaction was initiated in the manner similar to Example 2 and in the course of increasing the propylene and air supplies and decreasing the nitrogen supply, at the point of time when respective flow rates became 3.8 m³ (STP)/hr of propylene, 35.2 m³ (STP)/hr of air and 8.7 m³ (STP)/hr of nitrogen, the maximum peak temperature of the catalyst layers in the second reaction zones rose to 415° C. in some of the reaction tubes. The propylene supply however was maintained at the same rate and consequently the sum of each ΔT at the catalyst layer in each of the reaction zones got to 185° C. By that time about 50 hours had passed since the initiation of propylene supply, whereat the maximum peak temperature in the second reaction zones was 428° C., and that in the first reaction zones was 397° C. Thereafter the propylene supply rate was increased up to the target value similarly to Example 2 to attain the prescribed reaction conditions and the start-up was completed. By that time 135 hours had passed since the initiation of propylene supply. The heating medium temperature then was 326° C., the maximum peak temperature of the catalyst layers was 410° C. and the sum of each ΔT at the catalyst layer in each of the reaction zones was 164° C. The propylene conversion was 97.6% and acrolein and acrylic acid yield was 93.0%. Compared with Example 2, the catalytic performance at the time when the prescribed reaction conditions were reached was low.

Example 3

[Reactor]

A reactor composed of a steel reaction tube of 3000 mm in total length and 25 mm in inner diameter, a shell for passing a heating medium therethrough and for covering the reaction tube, and a temperature measuring device comprising a thermocouple having a temperature-detection part for measuring temperature in the reaction tube, said thermocouple being freely mobile along the axial direction in the tube, was set vertically, and the temperatures of the catalyst layers were regularly monitored. From the top of the reactor the catalyst 2, catalyst 4 and catalyst 1 were dropped by the order stated, to form the first reaction zone (a catalyst layer loaded with catalyst 2), the second reaction zone (a catalyst layer loaded with catalyst 4) and the third reaction zone (a catalyst layer loaded with catalyst 1). The respective layer lengths were 150 mm, 800 mm and 2000 mm. The propylene conversion and acrolein and acrylic acid yield were monitored by continuously sampling the gas at the inlet of the reactor and that at the outlet of the reactor and analyzing them by online gas chromatography.

[Oxidation]

The temperature of the heating medium was maintained at 323° C., and into the catalyst-loaded reaction tube a gaseous mixture of 1.33 m³ of air (STP)/hr, 0.61 m³ of nitrogen (STP)/hr and 0.29 m³ (STP)/hr of steam was supplied from the bottom end of the reactor. Subsequently propylene supply was started in such a manner as to attain its supply rate of 0.136 m³ (STP) hr after 3 hours. The composition of the reactant gas at that time was: propylene 5.8 vol %, oxygen 11.8 vol %, steam 12.1 vol % and the balance of an inert gas such as nitrogen. The propylene conversion was 97.9% and acrolein and acrylic acid yield was 93.9%. The respective maximum peak temperatures of the catalyst layers in the reaction zones were 337° C. in the first reaction zone, 384° C. in the second reaction zone, and 367° C. in the third reaction zone, and the sum of each ΔT at the catalyst layer in each of the reaction zones was 119° C.

Then the temperature of the heating medium was changed to 328° C. In the course of increasing the propylene and air supplies and decreasing the nitrogen supply, when the respective flow rates became 0.164 m³ (STP)/hr of propylene, 1.53 m³ (STP)/hr of air and 0.378 m³ (STP)/hr of nitrogen, the respective maximum peak temperatures of the catalyst layers in the first and third reaction zones were 343° C. and 386° C. Whereas, the maximum peak temperature of the catalyst layer in the second reaction zone rose to 428° C. and was about to exceed 450° C., and the heating medium temperature was changed to 319° C. Up to that time about 32 hours had passed since the initiation of propylene supply, and the composition of the reactant gas then was: propylene 6.9 vol %, oxygen 13.6 vol %, steam 12.1 vol %, and the balance of an inert gas such as nitrogen. The propylene conversion was 98.3% and the acrolein and acrylic acid yield was 94.3%. The maximum peak temperature of the catalyst layer in the second reaction zone temporarily rose to 432° C., and the sum of each ΔT at the catalyst layer in each of the reaction zones was 177° C.

In the course of increasing the propylene and air supplies and decreasing the nitrogen supply while keeping the heating medium temperature of 319° C., at the point when the respective flow rates became 0.185 m$^3$ (STP)/hr of propylene, 1.70 m$^3$ (STP)/hr of air and 0.195 m$^3$ (STP)/hr of nitrogen, the propylene conversion was about to drop below 90%. Accordingly, after 40 hours from the initiation of propylene supply, the nitrogen flow rate was changed to 0.130 m$^3$ (STP)/hr and the heating medium temperature was raised to 324° C. to increase the propylene supply. The propylene supply rate after the time passage of 48 hours was 0.190 m$^3$ (STP)/hr, the composition of the reactant gas was: propylene 8.3 vol %, oxygen 15.4 vol %, steam 12.4 vol % and the balance of an inert gas such as nitrogen, the propylene conversion was 98.2%, acrolein and acrylic acid yield was 94.2%, respective maximum peak temperatures of the catalyst layers were 339° C. in the first reaction zone, 408° C. in the second reaction zone and 382° C. in the third reaction zone, and the sum of each ΔT at the catalyst layer in each of the reaction zones was 157° C.

Further increasing the propylene supply rate up to the target value of 0.197 m$^3$ (STP)/hr, the prescribed reaction conditions were reached to complete the start-up. The composition of the reactant gas then was propylene 8.3 vol %, oxygen 15.0 vol %, steam 12 vol % and the balance of an inert gas such as nitrogen.

Throughout the start-up stage, the propylene conversion of at least 90 mol % was maintained, the maximum peak temperatures of the catalyst layers in all of the reaction zones were maintained below 450° C., and the sum of each ΔT at the catalyst layer in each of the reaction zones, not more than 180° C.

By the completion of the start-up, 62 hours had passed since the initiation of propylene supply, whereat the propylene conversion was 97.8%, acrolein and acrylic acid yield was 93.8%, heating medium temperature was 326° C., and the respective maximum peak temperatures of the catalyst layers in the first to third reaction zones were 341° C., 410° C. and 385° C. The sum of each ΔT at the catalyst layer in each of the reaction zones was 158° C.

Example 4

[Preparation of Catalyst 5 and Catalyst 6]

The acrolein-oxidizing catalysts which were used for production of acrylic acid by catalytic vapor-phase oxidation of acrolein (hereafter referred to as "second stage catalysts") were prepared following the method described in Example 1 of JP2005-120079A. The composition of these catalysts excluding oxygen and the carrier in terms of atomic ratios was $Mo_{12}V_5W_1Cu_2Sb_{0.5}$.

Catalyst 5: Spherical silica-alumina of 8 mm in average particle diameter was uses as the carrier.
Catalyst 6: Spherical silica-alumina of 5 mm in average particle diameter was used as the carrier.

[Reactor]

Two reactors each composed of a steel reaction tube of 3000 mm in total length and 25 mm in inner diameter, a shell for passing a heating medium therethrough and for covering the reaction tube, and a temperature measuring device comprising a thermocouple having a temperature-detection part for measuring temperature in the reaction tube, said thermocouple being freely mobile along the axial direction in the tube, were vertically set in series. From the top of the first reactor the catalyst 4 and catalyst 1 were successively dropped to form the first reaction zone (a catalyst layer loaded with catalyst 4) and the second reaction zone (a catalyst layer loaded with catalyst 1), the respective layer lengths in the reaction zones being 850 mm and 2050 mm. Also from the top of the second reactor the catalyst 5 and catalyst 6 were successively dropped to form the third reaction zone (a catalyst layer loaded with catalyst 5) and the fourth reaction zone (a catalyst layer loaded with catalyst 6), making the respective layer lengths in the reaction zones 800 mm and 2100 mm. The top end of the first reactor and the bottom end of the second reactor were connected with piping.

The propylene conversion and acrolein and acrylic acid yield were monitored by continuously sampling the gas at the inlet and outlet of the first reactor and that at the outlet of the second reactor and analyzing them by online gas chromatography to determine the amounts of propylene, acrolein and acrylic acid in each of the reactant gases.

For each of the reactors the heating medium temperature was separately controlled, and the respective catalyst layer temperatures were regularly monitored.

[Oxidation]

The heating medium temperature was kept at 324° C. for the first reactor and at 267° C. for the second reactor. Into the first reactor a gaseous mixture of 1.28 m$^3$ (STP)/hr of air, 0.583 m$^3$ (STP)/hr of nitrogen and 0.274 m$^3$ (STP)/hr of steam was fed from the bottom end of the reaction tube. Subsequently propylene supply was started in such a manner as to attain its supply rate of 0.133 m$^3$ (STP)/hr after 3 hours. The composition of the reactant gas at that time was: propylene 5.9 vol %, oxygen 11.8 vol %, steam 12.1 vol % and the balance of an inert gas such an nitrogen. The respective maximum peak temperatures of the catalyst layers in the first reactor were 389° C. in the first reaction zone, and 369° C. in the second reaction zone, and the sum of each ΔT at the catalyst layer in each of the reaction zones was 110° C. The propylene conversion and acrolein and acrylic acid yield at the outlet of the first reactor were 97.9% and 94.0%, respectively. The respective maximum peak temperatures of the catalyst layers in the second reactor were 334° C. in the third reaction zone and 297° C. in the fourth reaction zone. The sum of each ΔT at the catalyst layer in each of the reaction zones was 93° C., and the acrylic acid yield at the outlet of the second reactor was 87.9%.

Then the heating medium temperature in the first reactor was changed to 328° C. and that in the second reactor, to 268° C. In the course of gradually increasing the propylene and air supplies and gradually decreasing the nitrogen supply, at the point of time when the respective flow rates became 0.156 m$^3$ (STP)/hr of propylene, 1.48 m$^3$ (STP)/hr of air and 0.364 m$^3$ (STP)/hr of nitrogen, the maximum peak temperature of the catalyst layer in the second reaction zone of the first reactor was 387° C., but that in the first reaction zone rose to 424° C. and was about to exceed 450° C. Whereupon the temperature of the heating medium in the first reactor was changed to 320° C. Up to that time about 30 hours had passed since the initiation of propylene supply, and the composition of the reactant gas then was: propylene 6.9 vol %, oxygen 13.6 vol %, steam 12.1 vol %, and the balance of an inert gas such as nitrogen. The maximum peak temperature of the catalyst layer in the first reaction zone of the first reactor temporarily rose to 431° C., and the sum of each ΔT at the catalyst layer in each of the reaction zones was 162° C. At the outlet of the first reactor, the propylene conversion was 98.0%, and acrolein and acrylic acid yield was 94.1%. The maximum peak temperatures of the catalyst layers of the reaction zones in the second reactor were 352° C. at the third reaction zone and 320° C. in the fourth reaction zone, respectively. The sum of each ΔT at the catalyst layer in each of the reaction zones was 136° C., and the acrylic acid yield at the outlet of the second reactor was 88.0%.

Further gradually raising the heating medium temperature, gradually increasing the propylene and air supplies and gradually decreasing the nitrogen supply, the respective flow rates meeting the prescribed reaction conditions of 0.187 m³ (STP)/hr of propylene (the target value), 1.61 m³ (STP)/hr of air and 0.21 m³ (STP)/hr of nitrogen were attained, to complete the start-up. Until the completion, 63 hours had passed since the initiation of propylene supply. The heating medium temperatures then were 325° C. for the first reactor and 271° C. for the second reactor. The composition of the starting reactant gas was: propylene 8.2 vol %, oxygen 14.8 vol %, steam 12 vol %, and the balance of an inert gas such as nitrogen. The respective maximum peak temperatures of the catalyst layers in the first reactor were 415° C. in the first reaction zone, and 382° C. in the second reaction zone, and the sum of each ΔT at the catalyst layer in each of the reaction zones was 147° C. The propylene conversion and acrolein and acrylic acid yield at the outlet of the first reactor were 98.0% and 94.1%, respectively. The respective maximum peak temperatures of the catalyst layers in the second reactor were 355° C. in the third reaction zone and 324° C. in the fourth reaction zone. The sum of each ΔT at the catalyst layer in each of the reaction zones was 137° C., and the acrylic acid yield at the outlet of the second reactor was 88.0%.

Throughout the start-up stage, propylene conversion of at least 90 mol % was maintained, the maximum peak temperatures of the catalyst layers in both reaction zones in the first reactor were maintained below 450° C., and the sum of each ΔT at the catalyst layer in each of the reaction zones, below 180° C. The maximum peak temperatures of the catalyst layers in both reaction zones in the second reactor were not higher than 400° C., and the sum of each ΔT at the catalyst layer in each of the reaction zones never exceeded 150° C.

Thereafter the steady state (standard operation conditions) was maintained while controlling the temperatures of the heating media to keep the propylene conversion of at least 97%, and the reaction was continued for 4,000 hours. After the 4000 hours passed, the temperature of the heating medium for the first reactor was 334° C., the respective maximum peak temperatures of the catalyst layers in the first and second reaction zones were 416° C. and 395° C., the sum of each ΔT at the catalyst layer in each of the reaction zones was 143° C., and the propylene conversion at the outlet of the first reactor was 97.8%, and the acrolein and acrylic acid yield was 93.6%. Whereas, the temperature of the heating medium for the second reactor was 277° C., the respective maximum peak temperatures of the catalyst layers in the third and fourth reaction zones were 358° C. and 329° C. The sum of each ΔT at the catalyst layer in each of the reaction zones was 133° C., and the acrylic acid yield at the outlet of the second reactor was 87.3%.

The invention claimed is:

1. A process for producing acrolein and acrylic acid by catalytic vapor-phase oxidation of propylene or a propylene-containing gas with molecular oxygen or a molecular oxygen-containing gas, comprising:
    loading a fixed bed reactor with a catalyst in such a manner that at least two layers reaction zones having different catalytic activity are formed in an axial direction of each reaction tube,
    wherein a propylene supply rate is increased in a start-up stage of the reaction until a prescribed composition of a starting reactant gas and a flow rate of the starting reactant gas are attained, while adjusting at least one of a reaction temperature, the composition of the starting reactant gas and the flow rate of the starting reactant gas, so as to maintain a propylene conversion at not lower than 90 mol%, a maximum peak temperature of a catalyst layer in each reaction zone at no higher than 450° C., and a sum of each ΔT(maximum peak temperature of a catalyst layer—reaction temperature) at the catalyst layer in each reaction zone to be no more than 180° C., respectively.

2. The process according to claim 1, wherein the fixed bed reactor is loaded with the catalyst in such a manner that the catalytic activity in the reaction zones successively rises from a starting gas inlet side toward an outlet side.

3. The process according to claim 1, in which the catalytic vapor-phase oxidation is carried out at a propylene space velocity of at least 110 hr$^{-1}$ (STP) under a steady state.

4. The process according to claim 2, in which the catalytic vapor-phase oxidation is carried out at a propylene space velocity of at least 110 hr$^{-1}$ (STP) under a steady state.

* * * * *